United States Patent [19]

Van Den Elshout

[11] Patent Number: 5,776,453
[45] Date of Patent: Jul. 7, 1998

[54] DEODORANT COMPOSITION CONTAINING A COMPOUND WHICH YIELDS FORMALDEHYDE

[76] Inventor: Wilhelmus Hendricus Hubertus Van Den Elshout, Onderstehof 9, NL-6132 SM Sittard, Netherlands

[21] Appl. No.: 693,331

[22] PCT Filed: Jan. 30, 1995

[86] PCT No.: PCT/NL95/00043

§ 371 Date: Aug. 15, 1996

§ 102(e) Date: Aug. 15, 1996

[87] PCT Pub. No.: WO95/22309

PCT Pub. Date: Aug. 24, 1995

[30] Foreign Application Priority Data

Feb. 18, 1994 [NL] Netherlands .................. 9400260

[51] Int. Cl.⁶ .................. A61K 7/32; A61K 7/00; A01N 25/02
[52] U.S. Cl. .................. 424/65; 424/400; 424/401; 424/404
[58] Field of Search .................. 424/400, 401, 424/404, 65

[56] References Cited

FOREIGN PATENT DOCUMENTS

| | | |
|---|---|---|
| 8 299 | 11/1970 | France . |
| 2 302 083 | 9/1976 | France . |
| 2 443 838 | 7/1980 | France . |
| 58-012654 | 1/1983 | Japan . |
| 507323 | 4/1976 | U.S.S.R. . |
| 534237 | 1/1977 | U.S.S.R. . |

OTHER PUBLICATIONS

Database EPODOC, CN-A-1062838, Jul. 22, 1992.

STN International, Karlsruhe, File Chemical Abstracts, AN=122:273803 & CN.A.1088084, Jun. 22, 1994.

Rote Liste, Bundesverband der Pharmazeutischen Industrie E.V., Editio Cantor, Aulendorf, 1993, No. 31218 "Antihydral".

Reynolds, J.E.F., *Martindale, The Extra Pharmacopoeia*, 29th Edition, 1989, The Pharmaceutical Press, London, pp. 246–247.

*Primary Examiner*—Shelley A. Dodson
*Attorney, Agent, or Firm*—Young & Thompson

[57] ABSTRACT

The invention relates to a product for preventing and controlling bad smells caused by human perspiration containing at least one compound (a) which yields an aldehyde, in particular formaldehyde, under the influence of human perspiration fluid, wherein compound (a) is preferably selected from hexamethylene tetramine (HMTA), para-formaldehyde and trioxane, the use of compound (a) as well as a container containing product (a) in the form of a liquid preparation.

5 Claims, No Drawings

DEODORANT COMPOSITION CONTAINING A COMPOUND WHICH YIELDS FORMALDEHYDE

The present invention relates to a product for preventing and controlling bad smells caused by human perspiration, e.g. smells coupled with perspiring (sweaty) feet. Such smells are caused by decomposition products produced by bacteria. Such decomposition products of human perspiration fluid may be bad smelling acids.

It is an object of the present invention to provide a product which is effective for combatting cause and effect of such decomposition products.

A further object of the invention is to provide products as mentioned in the preamble in the form which is easy to use.

According to the invention these objects are realized by a product as mentioned in the preamble, which product contains at least one compound (a) which yields an aldehyde, in particular formaldehyde, under the influence of human perspiration fluid.

In general compound (a) consists of hexamethylene tetramine or any other cyclic formaldehyde ammonia or urea condensation product, or polymeric formaldehyde compound like para-formaldehyde and trioxane.

Preferably, compound (a) is selected from hexamethylene tetramine (HMTA), paraformaldehyde and trioxane. HMTA is especially preferred.

In the product according to the invention compound (a), e.g. HMTA, is present in an amount of 0.005–1 wt. %, preferably 0.01–0.15 wt. %, calculated on the weight of the total product. If the amount of compound (a) is less than 0.005 wt. %, the effect of the product is too low. Higher amounts than 1 wt. % may be used, but this is not 30 necessary in e.g. liquid preparations such as foot sprays.

The product according to the invention may be present in various forms, i.e. in the form of a cosmetic preparation or in other forms, which are illustrated hereinbelow.

According to a preferred embodiment the product is present in a liquid form, e.g. in the form of a clear solution. Such liquid preparations may contain usual additives, solvents, and/or diluents. Preferably such liquid preparation contains one or more physiologically acceptable solvents and/or diluents selected from water and alcohols, such as ethanol, isopropanol and glycerol.

According to the preferred embodiment the invention provides a preparation destined for the treatment of feet, which composition contains compound (a), e.g. HMTA, camphor as an additive and water and ethanol as solvents.

In case the product of the invention contains e.g. HMTA, the aimed effect seems to be based on the slow production of formaldehyde from HMTA under the influence of organic acids present in perspiration fluid or formed by virtue of bacterial action (e.g. butyric acid).

The effect of the composition of the invention can be increased by adding formaldehyde and/or camphor. Camphor is a disinfectant and strengthens the action of the product. Furthermore camphor has a hardening effect on the skin of the feet providing a drier feeling of the feet.

According to a special embodiment of the invention the aldehyde and/or camphor are present in amounts of 0.001–0.05 wt. % and 0.1–30 wt. % respectively, calculated on the weight of the total product.

If in the product of the invention glycerol is used, then the amount thereof will be preferably 1–15 wt. %, calculated on the weight of the total product.

An example of a composition according to the invention, suitable for application on the human skin, in particular feet, comprises for example 40–60 wt. % of water
1–30 wt. % of camphor
40–60 wt. % of ethanol
30–15 wt. % of glycerol
0.05–0.15 wt. % of hexamethylene tetramine
0.01–0.05 wt. % of formaldehyde, all amounts calculated on the weight of the total product. Of course, the total amount of the various components cannot exceed 100 wt. %.

As mentioned in the above the product of the invention may be present in the form of a clear solution. Such a solution can be easily atomized with or without an added propellant and directly applied onto e.g. feet, but also on socks, insoles, shoes and the like. Of course, the liquid composition according to the invention can be in any suitable cosmetic form, which is generally known for anti-perspiration agents.

The invention also relates to a container containing the product as described in the above, preferably in the form of a clear solution, which container is provided with means to atomize the liquid preparation. In particular, a so-called pump atomizer is used. Such a container may have a content of 0.01–1 litre, preferably 0.02–0.4 litre.

If the liquid preparation of the invention is used for the treatment of feet, it is preferred to spray the preparation onto the foot soles and, if desired, the shoes or its insoles during a period of 3–5 days. It is sufficient to spray once a day. After such a period the frequency of the treatment can be reduced to a few times a month.

With reference to the above the invention also relates to a product containing compound (a) suitable to be worn on a part of the human body where perspiration occurs, such as socks, insoles and shoes.

The invention relates to the use of compound (a) for preventing and controlling bad smells caused by human perspiration and for the preparation of products suitable for preventing and controlling such smells.

EXAMPLE

Composition of a solution according to the invention.

In a glass jar the following ingredients are added under stirring: 450 parts by weight of ethanol, 50 parts by weight of camphor, 40 parts by weight of glycerol, 1.3 parts by weight of formaldehyde (37 wt. % in water), 1.5 parts by weight HMTA and 450 parts by weight of water. The so obtained solution is clear and can be immediately used.

Panel test

Five subjects of experiments having considerable problems relating to bad smells caused by perspiration of their feet used the solution of the example once a day during a period of 5 days. During this use also the insoles of their shoes were well sprayed in by means of a pump atomizer. After five days the bad smells had completely disappeared. In order to continued this effect they had to repeat the treatment once in 10 days (average value).

I claim:

1. Product for preventing and controlling malodors caused by human perspiration containing
   a. 0.005–0.15 wt. % of a compound selected from the group consisting of formaldehyde, para-formaldehyde and trioxane,
   b. 0.01 –0.15 wt. % of hexamethylene tetramine and,
   c. 0.1–30 wt. % of camphor,
   wherein said amounts are based on the weight of the total product.

2. The product according to claim 1 containing one or more physiologically acceptable solvents and/or diluents selected from water and alcohol.

3. The product according to claim 2 in the form of a clear solution, comprising
- 40–60 wt. % of water
- 1–30 wt. % of camphor
- 40–60 wt. % of ethanol
- 1–15 wt. % of glycerol
- 0.05–0.15 wt. % of hexamethylene tetramine
- 0.01–0.05 wt. % of formaldehyde, wherein all amounts are calculated on the weight of the total product, and the total amount is 100 wt. %.

4. Container containing a product according to claim 1 in the form of a liquid preparation, said container being provided with means to atomize the liquid preparation.

5. A product to be worn on the feet of a human, sprayed with the product of claim 1.

* * * * *